United States Patent
Chiapetta

(10) Patent No.: US 10,980,658 B2
(45) Date of Patent: Apr. 20, 2021

(54) NASAL SUPPORT DEVICE

(71) Applicant: FLAIR, LLC, Delano, MN (US)

(72) Inventor: James R. Chiapetta, Delano, MN (US)

(73) Assignee: Flair, LLC, Delano, MN (US)

( * ) Notice: Subject to any disclaimer, the term of this patent is extended or adjusted under 35 U.S.C. 154(b) by 123 days.

(21) Appl. No.: 16/012,630

(22) Filed: Jun. 19, 2018

(65) Prior Publication Data

US 2018/0360584 A1 Dec. 20, 2018

Related U.S. Application Data

(60) Provisional application No. 62/522,542, filed on Jun. 20, 2017.

(51) Int. Cl.
*A61F 5/08* (2006.01)
*A01K 29/00* (2006.01)

(52) U.S. Cl.
CPC ............... *A61F 5/08* (2013.01); *A01K 29/00* (2013.01)

(58) Field of Classification Search
CPC .... A61F 5/08; A61F 5/56; A61F 2013/00476; A61F 13/0259; A61F 13/0263; A61F 13/0266; A61F 13/0269; A61F 13/0273; A61F 13/0246; A61F 13/025; A61F 13/0253; A61F 13/0256; A61D 7/04; A61M 15/08; A61B 17/24; A61B 2017/246
USPC ............................................. 606/204.45, 199
See application file for complete search history.

(56) References Cited

U.S. PATENT DOCUMENTS

| | | |
|---|---|---|
| 5,913,873 A | 6/1999 | Blach et al. |
| 5,976,173 A | 11/1999 | Berke |
| 6,017,357 A | 1/2000 | Blach et al. |
| 6,033,422 A | 3/2000 | Blach et al. |
| 6,080,179 A * | 6/2000 | Gould ................ A61F 5/08 606/204.45 |
| 6,203,560 B1 | 3/2001 | Blach et al. |
| 6,352,548 B1 * | 3/2002 | Blach ................ A61D 7/04 128/200.24 |
| 6,676,681 B1 | 1/2004 | Blach et al. |
| 6,823,864 B2 | 11/2004 | Blach et al. |
| 7,175,645 B1 | 2/2007 | Blach et al. |
| 8,182,505 B2 | 5/2012 | Blach et al. |

(Continued)

OTHER PUBLICATIONS

International Search Report and Written Opinion issued in related International Patent Application No. PCT/US2018/038309 dated Oct. 4, 2018.

(Continued)

*Primary Examiner* — Katherine H Schwiker
*Assistant Examiner* — Alexis D Amechi
(74) *Attorney, Agent, or Firm* — Merchant & Gould P.C.

(57) ABSTRACT

A nasal support device includes a device body. The device body defines a perimeter shape of the nasal support device and also can include a nasal support structure. The nasal support device also includes adhesive carried with the device body. The nasal support device further includes a peelable backing that covers the adhesive and includes at least one peelable backing piece that is divided into a first section and a second section by a pre-defined fold location. The pre-defined fold location is configured such that the first and second sections of the peelable backing piece remain coupled together at the pre-defined fold location after folding at the pre-defined fold location.

5 Claims, 7 Drawing Sheets

(56) References Cited

U.S. PATENT DOCUMENTS

| | | | |
|---|---|---|---|
| 8,529,594 B2 | 9/2013 | Blach et al. | |
| 8,795,314 B2 | 8/2014 | Blach et al. | |
| 8,871,328 B2* | 10/2014 | Wyner | A41D 13/082 |
| | | | 428/156 |
| 9,017,360 B2 | 4/2015 | Blach et al. | |
| 2002/0134379 A1 | 9/2002 | Blach et al. | |
| 2004/0133234 A1 | 7/2004 | Blach et al. | |
| 2004/0138698 A1 | 7/2004 | Blach et al. | |
| 2004/0193210 A1 | 9/2004 | Blach et al. | |
| 2005/0020957 A1* | 1/2005 | Lebner | A61B 17/085 |
| | | | 602/42 |
| 2006/0036278 A1 | 2/2006 | Blach et al. | |
| 2006/0149311 A1 | 7/2006 | Blach et al. | |
| 2007/0208369 A1 | 9/2007 | Blach et al. | |
| 2007/0255309 A1 | 11/2007 | Guyuron et al. | |
| 2008/0312680 A1 | 12/2008 | Blach et al. | |
| 2010/0159192 A1* | 6/2010 | Cotton | A61F 13/022 |
| | | | 428/137 |
| 2012/0059406 A1 | 3/2012 | Blach et al. | |
| 2016/0262943 A1* | 9/2016 | Arbesman | A61F 5/028 |
| 2018/0353343 A1* | 12/2018 | Bergstrom | A61F 13/0259 |

OTHER PUBLICATIONS

ScreenShots, Flairstrips, "How to Apply FLAIR® Strips with Positioning Tab for Black, White, Pink and Turquoise Strips," YouTube Internet Video, https://www.youtube.com/watch?v=yO_c0XvresYHi (Jun. 13, 2015).

* cited by examiner

NASAL SUPPORT DEVICE

CROSS-REFERENCE TO RELATED APPLICATIONS

This application claims benefit of U.S. Patent Provisional Application No. 62/522,542, filed Jun. 20, 2017, which application is hereby incorporated by reference in its entirety.

TECHNICAL FIELD

The present disclosure relates generally to nasal support devices. More particularly, certain aspects of the present disclosure are applicable to nasal support devices for use on animals such as horses.

BACKGROUND

A variety of nasal support devices have been developed for supporting tissues overlying the nasal passages of subjects. Example nasal support devices for use in humans are disclosed by U.S. Pat. Nos. 5,533,503; 5,546,929; and 5,553,605. Nasal support devices for use with animals such as horses are disclosed by U.S. Pat. Nos. 9,017,360; 6,823,864; 6,352,548; and 6,676,681. Nasal support devices have been demonstrated to reduce nasal passage narrowing that can occur during breathing in both humans and animals. By resisting nasal passage narrowing, nasal support devices can assist in reducing fatigue and lung stress. While existing nasal support devices have proven to be effective for resisting nasal passage narrowing, improvements are needed. Specifically, nasal support devices that are easier to handle and easier to precisely apply to a nose are needed.

SUMMARY

Aspects of the present disclosure relate to nasal support devices having features and configurations that facilitate the handling and precise application of such devices. Other aspects of the disclosure relate to methods for efficiently and effectively handling nasal support devices and efficiently and effectively affixing such nasal support devices at precise locations corresponding to nasal passages in need of support. In certain examples, nasal support devices in accordance with the principles of the present disclosure have backing layers with configurations adapted to promote the effective handling and application of such devices. In certain examples, the backing layers can include one or more pre-defined fold locations.

Aspects of the present disclosure relate to nasal support devices. It will be appreciated that aspects of the present disclosure are applicable for nasal support devices designed for use with humans or animals. Example animals for which nasal support devices in accordance with the principles of the present disclosure may be used include performance animals, such as horses, camels and dogs. Throughout most of the disclosure, the nasal support devices disclosed herein are referenced with respect to horses. However, the features disclosed herein for facilitating the handling and application of nasal support devices are equally applicable to nasal support devices for humans as well as other performance animals, such as camels and dogs.

Nasal support devices in accordance with the principles of the present disclosure can have various components such as layers, adhesives, and nasal support structures. It will be appreciated that various examples of such components can be found in U.S. Pat. Nos. 9,017,360; 6,823,864; 6,352,548; and 6,676,681, which are hereby incorporated by reference in their entireties.

One aspect of the present disclosure relates to a nasal support device including a device body defining a perimeter shape of the nasal support device and including a nasal support structure. The nasal support device also includes an adhesive carried with the device body and a peelable backing that covers the adhesive. The peelable backing includes at least one peelable backing piece that is divided into a first section and a second section by a pre-defined fold location. The pre-defined fold location is configured such that the first and second sections of the peelable backing piece remain coupled together at the pre-defined fold location after folding at the pre-defined fold location.

Another aspect of the present disclosure relates to a method for applying a nasal support device to a nose. The method includes peeling a first section of a peelable backing piece from adhesive of the nasal support device. The method also includes folding the peelable backing piece along a pre-defined fold location such that the first section of the peelable backing piece is folded over a second section of the peelable backing piece. The method further includes grasping the nasal support device at a grasping location where the first and second sections of the peelable backing piece are pinched together. The method additionally includes adhering of the nasal support device to the nose while the nasal support device remains grasped at the grasping location. Once at least a portion of the adhesive of the nasal support device has been adhered to the nose, the grasping location is released and the second section of the peelable backing piece is unpeeled from the adhesive. The first section of the peelable backing piece can be used as a handle for unpeeling the second section of the peelable backing piece from the adhesive. The handle is advantageous because during the application process the adhesive and the second section of the peelable backing piece are facing toward the nose of the subject. Thus, absent using the first section of the peelable backing piece as a handle, the second section of the peelable backing piece would be difficult to access without disturbing the adhesive already adhered to the nose of the subject. Once the peelable backing piece has been entirely unpeeled, the remainder of the adhesive (e.g., the adhesive that had coincided with the location of the second section of the peelable backing piece) is adhered to the nose.

Another aspect of the present disclosure relates to a nasal support device including a device body defining a caudal edge positioned opposite from a rostral edge and a left edge positioned opposite from a right edge. The left and right edges each extend from the caudal edge to the rostral edge. The device also includes a medial portion positioned between left and right portions. The medial portion is located at a central region of the device body and has a length that extends from the caudal edge to the rostral edge. The left portion is located between the medial portion and the left edge and the right portion is located between the medial portion and the right edge. The device body also includes a nasal support structure. The nasal support device also includes adhesive carried with the device body. The adhesive includes medial adhesive corresponding to the medial portion of the device body, left adhesive corresponding to the left portion of the device body, and right adhesive corresponding to the right portion of the device body. The nasal support device further includes a peelable backing that covers the adhesive. The peelable backing has a multi-piece arrangement. The multi-piece arrangement includes a medial backing piece that covers the medial adhesive. The medial backing piece has a length that extends in a caudal-to-rostral orientation. The medial backing piece is divided into a caudal section and rostral section by a pre-defined fold location. The peelable backing also includes additional backing pieces that cover the left adhesive and the right adhesive. The pre-defined fold location is configured such that the caudal and rostral sections of the medial backing piece remain coupled together at the pre-defined fold location after folding at the pre-defined fold location.

A further aspect of the present disclosure relates to a method for applying a nasal support device to a nose. The method includes peeling one of a caudal section and a rostral section of a medial backing piece from adhesive of the nasal support device to provide a peeled medial backing section and a non-peeled medial backing section. The method also includes folding the medial backing piece along a pre-defined fold location such that the peeled medial backing section is folded over the non-peeled medial backing section. The method further includes grasping the nasal support device at a grasping location with the non-peeled medial backing section and the peeled medial backing section being pinched together at the grasping location. The method also includes peeling additional backing pieces from a left adhesive and a right adhesive of the nasal support device while the nasal support device remains grasped at the grasping location. The method also includes adhering the nasal support device to the nose while the nasal support device remains grasped at the grasping location. The method additionally includes releasing grasp from the nasal support device at the grasping location once a portion of the adhesive of the nasal support device has been adhered to the nose. Once the nasal support device has been released from the grasping location, the non-peeled medial backing section can be unpeeled from the adhesive. The peeled medial backing section can be used as a handle for unpeeling the non-peeled medial backing section from the adhesive. After the medial backing piece has been entirely unpeeled, the remainder of the adhesive of the nasal support device can be adhered to the nose.

A variety of additional aspects will be set forth in the description that follows. The aspects can relate to individual features and to combinations of features. It is to be understood that both the forgoing general description and the following detailed description are exemplary and explanatory only and are not restrictive of the broad inventive concepts upon which the examples disclosed herein are based.

DETAILED DESCRIPTION

Aspects of the present disclosure relate to nasal support devices having adhesive for securing such devices over the nasal passages of a subject, and also having at least one backing piece for covering the adhesive. The backing piece can be configured to facilitate handling the nasal support device and accurately and precisely adhesively affixing the nasal support device to a location on a nose corresponding to nasal passages desired to be supported. In certain examples, the at least one backing piece can include first and second backing piece sections separated by a pre-defined fold location. In certain examples, more than one pre-defined fold location can be provided. The pre-defined fold location allows one section of the backing piece to be folded relative to another section of the backing piece that remains covering the adhesive. The sections of the backing piece separated by the pre-defined fold location remain intact with one another after folding. The folded section provides a location where the nasal support device can be readily grasped for handling without contacting the adhesive. The folded configuration also allows the folded section of the backing piece to be used as a handle for unpeeling the previously unpeeled section of the backing piece after the nasal support device has been positioned and initially adhered to the nose.

Figure 1:
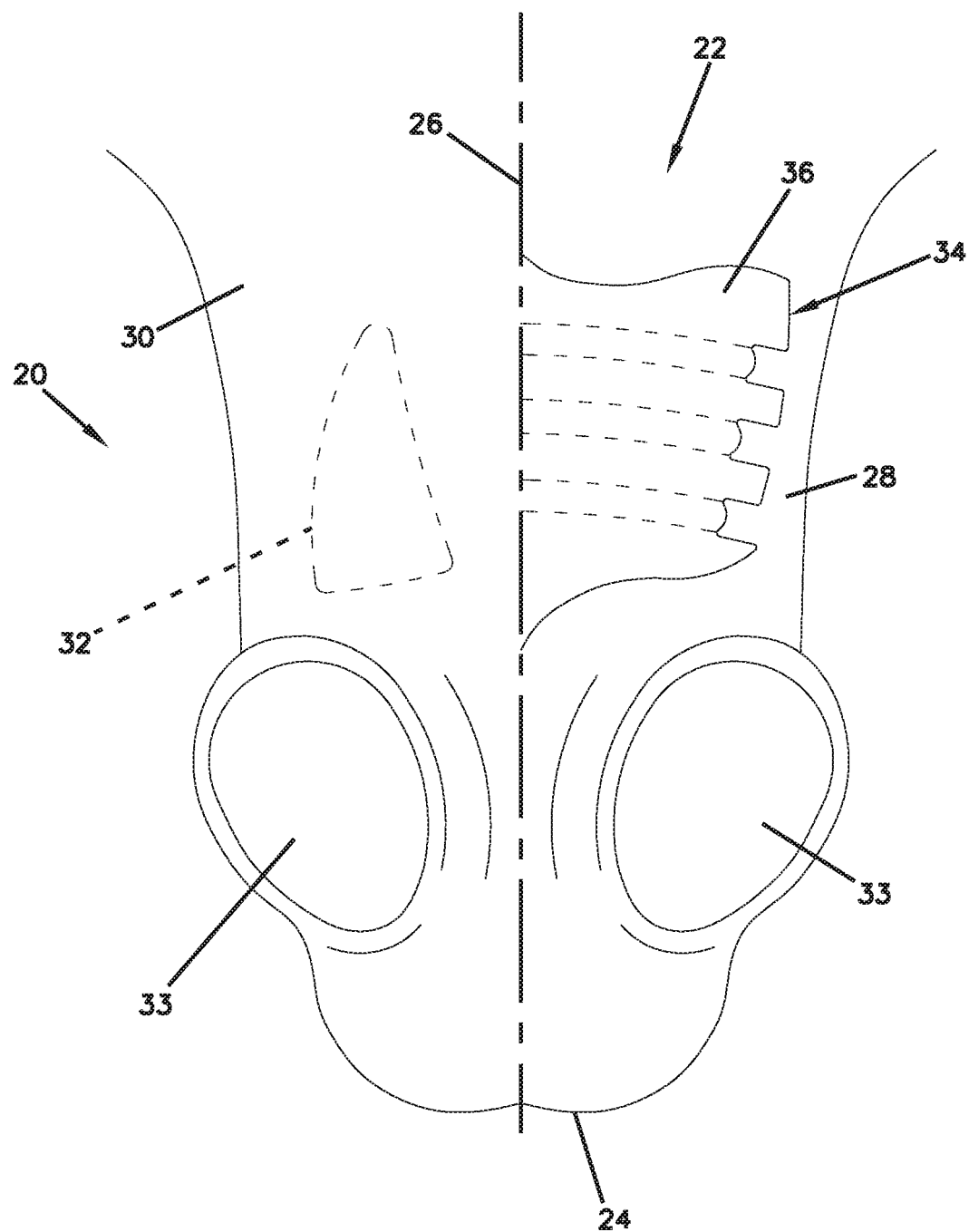
FIG. 1 is a diagrammatic representation of a nasal support device in accordance with the principles of the present disclosure secured to the nose of a horse. Only the left half of the nasal support device is depicted with the right half of the nasal support device having been intentionally omitted so that the right nasal passage of the horse's nose is readily visible.

FIG. 1 is a diagrammatic illustration of a nose 20 of a horse. The nose 20 includes a caudal end 22 and a rostral end 24. The nose 20 is shown bisected by a reference mid-line 26. The reference mid-line 26 divides the nose 20 into a left side 28 and a right side 30. Nostrils 33 are positioned on opposite sides of the reference mid-line 26. The nose 20 includes left and right nasal passages 32 respectively corresponding to the left and right sides 28, 30 of the nose 20. Only the location of tissue over the right nasal passage 32 is shown. To support the nasal passages 32, it is desirable to position a nasal support device 34 on the nose 20 directly over the nasal passages 32. It is preferred for the nasal support device 34 to be aligned along the reference mid-line 26 with a left side 36 of the nasal support device 34 positioned directly over the left nasal passage 32 (not shown) and a right side (not shown) of the nasal support device 34 positioned over the right nasal passage 32. Aspects of the present disclosure relate to features and methods for facilitating positioning and accurately aligning nasal support devices with the nasal passages, preferably centered along a mid-line of the subject's nose. Aspects of the present disclosure also relate to arrangements that allow for the effective handling and application of nasal support devices without touching or contaminating the underlying adhesive.

Figure 2:
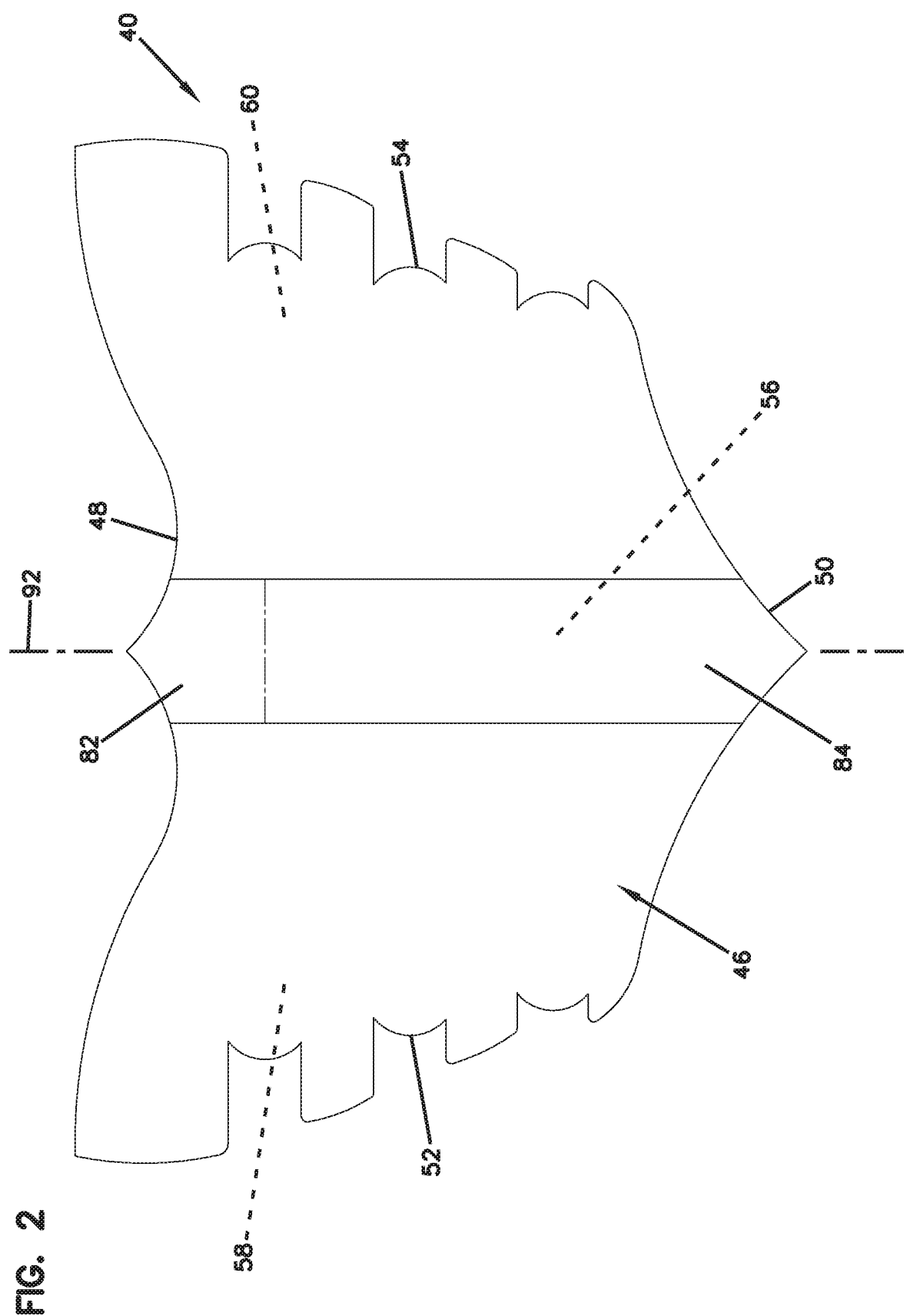
FIG. 2 is a bottom, plan view of a nasal support device in accordance with the principles of the present disclosure.
Figure 3:
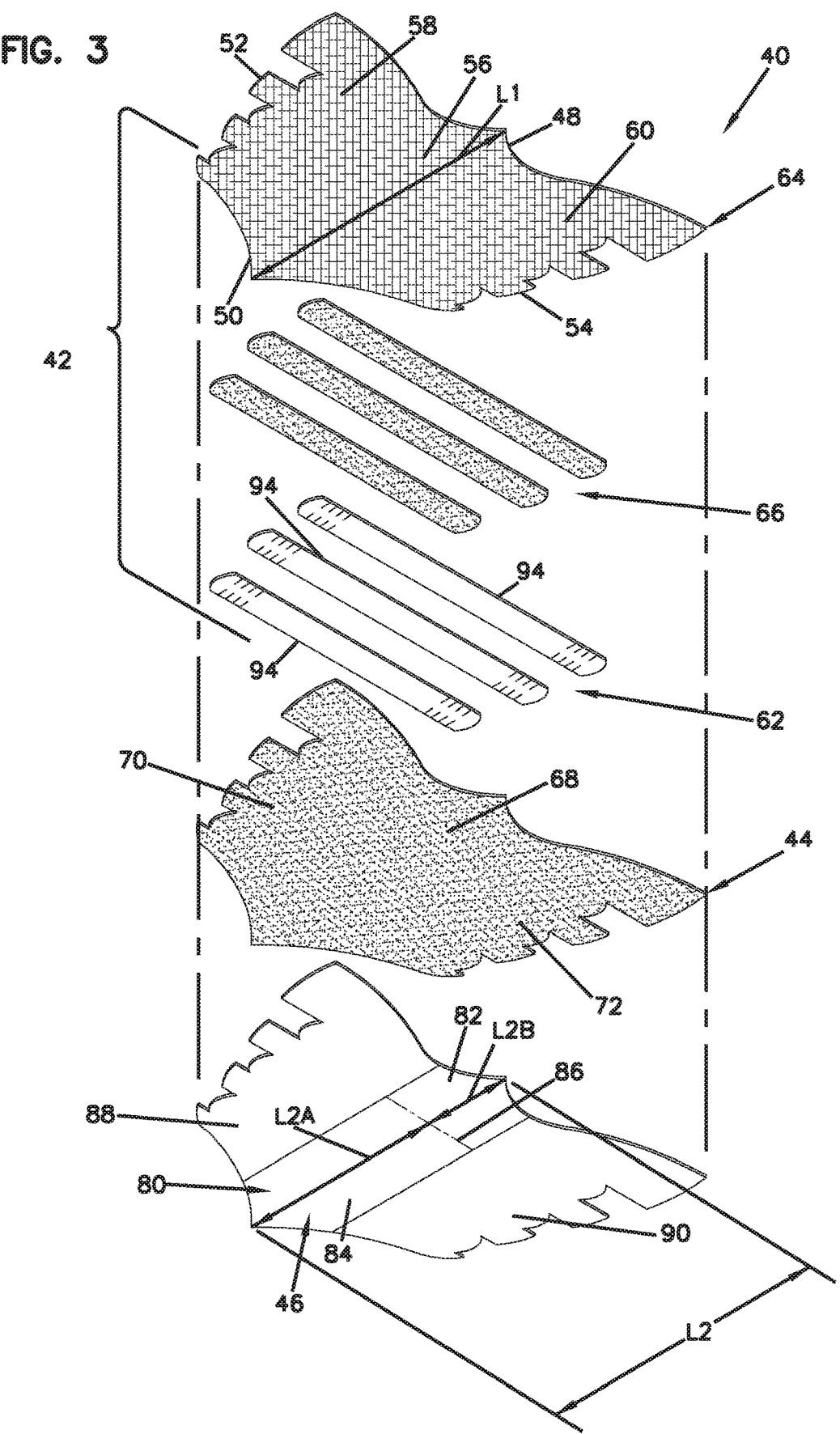
FIG. 3 is an exploded view of the nasal support device of FIG. 2.

FIGS. 2 and 3 show one example of a nasal support device 40 in accordance with the principles of the present disclosure. The nasal support device 40 includes a device body 42, adhesive 44 carried with the device body 42 for adhering the nasal support device 40 to the nose of a subject, and a peelable backing 46 that covers the adhesive 44 until it is desired to adhere the nasal support device 40 to the nose of a subject.

The device body 42 defines a caudal edge 48 positioned opposite from a rostral edge 50 and left edge 52 positioned opposite from a right edge 54. The device body also includes a medial portion 56 positioned between left and right portions 58 and 60. The medial portion 56 is located at a central region of the device body and has a length L1 that extends from the caudal edge 48 to the rostral edge 50. The left portion 58 is located between the medial portion 56 and the left edge 52. The right portion 60 is located between the medial portion 56 and the right edge 54. It will be appreciated that there is no distinct delineation between the medial portion 56, the left portion 58, and the right portion 60. Instead, such portions represent general areas of the device body 42.

The device body also includes a nasal support structure 62. The nasal support structure 62 is secured (e.g., adhered) to a layer 64 of the device body 42 by means such as adhesive 66. The layer 64 can be configured to define the caudal edge 48, the rostral edge 50, the left edge 52 and the right edge 54 of the device body 42. In certain examples, the layer 64 can also be configured as a substrate for carrying at least some of the adhesive 44.

The adhesive 44 is carried with the device body 42. The adhesive 44 includes medial adhesive 68 corresponding to the medial portion 56 of the device body 42, left adhesive 70 corresponding to the left portion 58 of the device body 42, and right adhesive 72 corresponding to the right portion 60 of the device body 42. It will be appreciated that no distinct delineation need be provided between the medial adhesive 68, the left adhesive 70 and the right adhesive 72. Rather, the medial, left and right designations merely indicate general areas of the adhesive 44.

The peelable backing 46 is adapted to cover the adhesive 44. The peelable backing as depicted has a multi-piece arrangement. Other examples of the peelable backing 46 may only include one piece. The multi-piece arrangement includes a medial backing piece 80 that covers the medial adhesive 68. The medial backing piece 80 has a length L2 that extends in a caudal-to-rostral orientation. In the example, L1 and L2 can be equal. The medial backing piece 80 is divided into a caudal section 82 and a rostral section 84 by a pre-defined fold location 86. The peelable backing 46 is depicted as also including additional backing pieces in addition to the medial backing piece 80. In particular, the peelable backing 46 is depicted as including a left backing piece 88 that covers the left adhesive 70 and a right backing piece 90 that covers the right adhesive 72. The pre-defined fold location 86 is configured such that the caudal and rostral sections 82, 84 of the medial backing piece 80 remain coupled together at the pre-defined fold location 86 after folding at the pre-defined fold location 86.

In certain examples, the rostral section 84 of the medial backing piece 80 has a length L2A that is longer than a length L2B of the caudal section 82 of the medial backing piece 80 as measured along the length L2. In certain examples, the length L2A of the rostral section 84 of the medial backing piece 80 is at least twice as long or at least three times as long as the length L2B of the caudal section 82 of the medial backing piece 80. In still other examples, the lengths L2A, L2B can be equal or length L2B can be longer than the length L2A.

As indicated above, in addition to the medial backing piece 80, the peelable backing 46 can include the left backing piece 88 and the right backing piece 90. The medial backing piece 80 is shown separating the left backing piece 88 from the right backing piece 90. It is preferred for each of the left backing piece 88, the right backing piece 90, and the medial backing piece 80 to be separately peelable from the adhesive 44.

As shown at FIG. 2, a reference mid-line 92 of the nasal support device 40 extends in the caudal-to-rostral orientation along the medial portion of the device body 42 and bisects the nasal support device 40. In certain examples, nasal support device 40 is optionally symmetric about the reference mid-line 92.

In certain examples, the nasal support structure 62 extends laterally across the medial portion 56 of the device body 42 and at least partially laterally across the left and right portions 58, 60 of the device body 42. As depicted, the nasal support structure 62 optionally includes a plurality of support members 94 having lengths that extend between the left and right edges 52, 54 of the device body 42. In the depicted example of FIG. 3, the support members 94 include three support members that are parallel to one another and that are spaced from one another along the caudal-to-rostral orientation. As indicated above, the device body 42 also includes the layer 64 that defines an outer boundary of the nasal support device 40 and serves as a substrate for carrying at least the portion of the adhesive 44 for use in adhering of the nasal support device 40 to the nose of a subject. In certain examples, the support members 94 are attached to the layer 64 either directly or indirectly. As depicted, the support members 94 are affixed directly to the layer 64 by the adhesive 66.

In certain examples, the nasal support device 40 can be arranged and configured for providing nasal support to the nasal passages of a horse. In certain examples, the device body 42 can have a maximum dimension in the caudal-to-rostral orientation in the range of 8-12 centimeters and a maximum dimension in the lateral orientation in the range of 10-17 centimeters. These maximum dimensions are particularly suited for a horse. Of course, for other subjects, different dimensions can be utilized.

Figure 4:
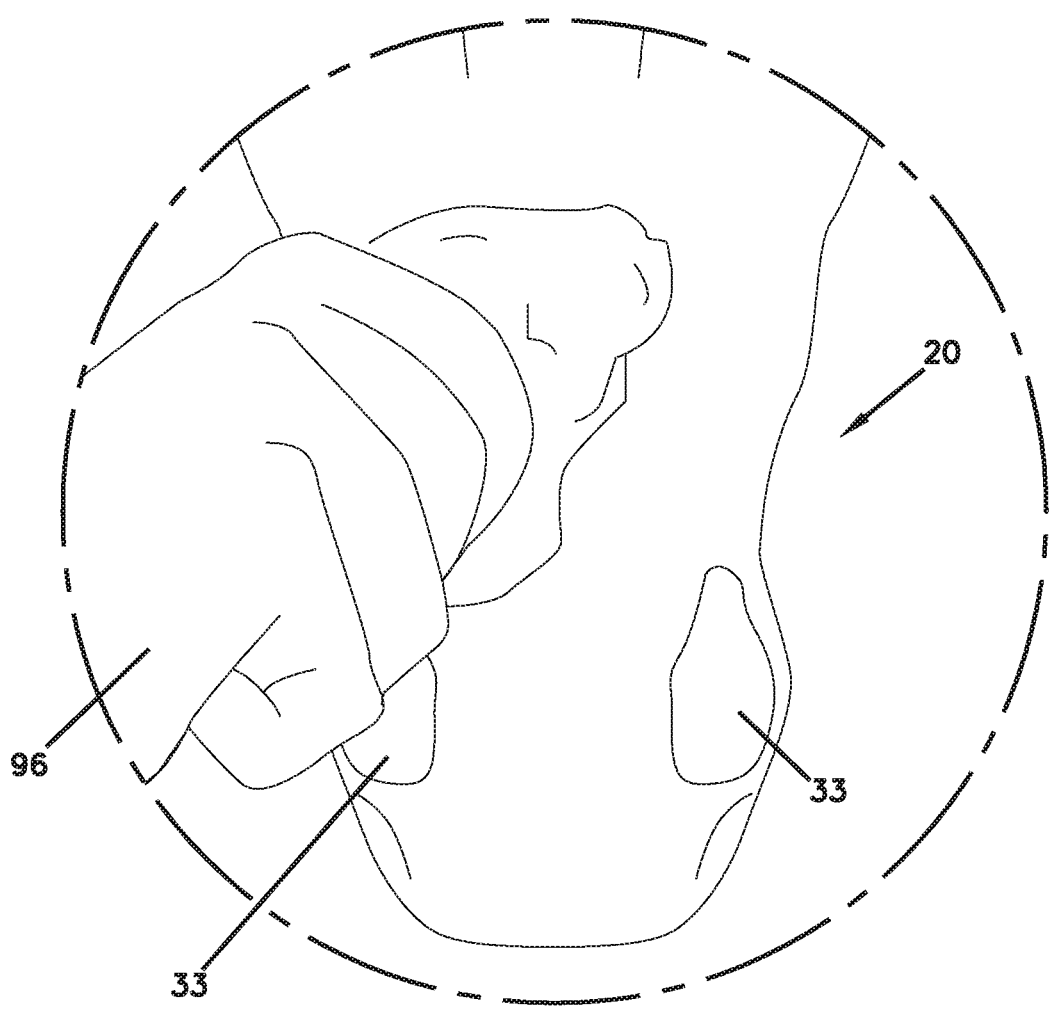
FIG. 4 shows the nose of a horse being cleaned prior to a nasal support device in accordance with the principles of the present disclosure being applied thereto.

Before applying the nasal support device 40 to the nose 20, the nose 20 is preferably first cleaned and dried as depicted in FIG. 4. Cleaning the nose 20 can involve a user 96 wiping the nose 20 above the nostrils 33 as shown in FIG. 4. Drying the nose 20 can involve letting the nose 20 air dry or wiping the nose 20 dry. For better application of the nasal support device 40, hair on the nose 20 can also be brushed upward (i.e., in the caudal direction).

Figure 5:
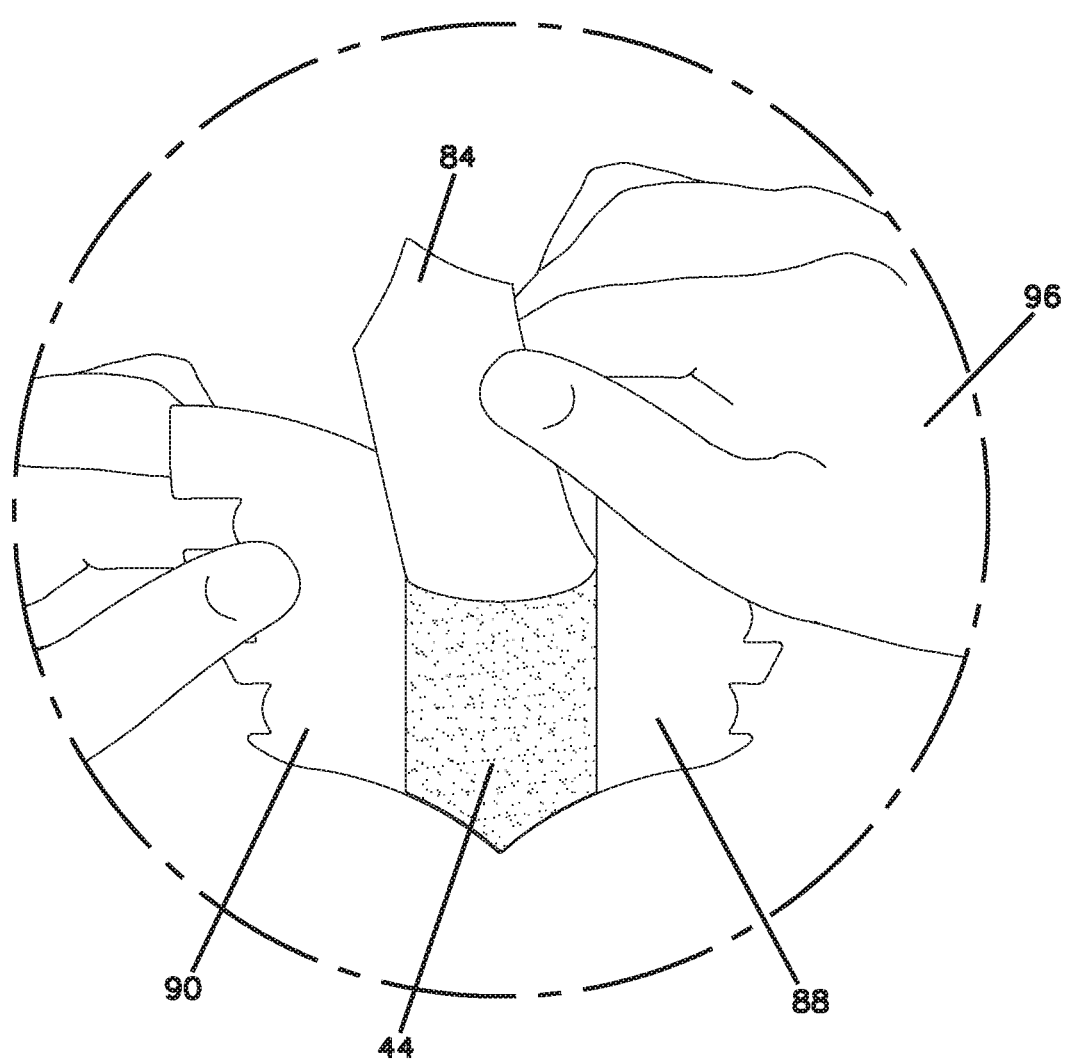
FIG. 5 shows a portion of a backing piece of the nasal support device in accordance with the principles of the present disclosure being unpeeled and folded relative to another portion of the backing piece that remains covering the underlying adhesive.

The nasal support device 40 can be applied to the nose 20 by peeling one of the caudal section 82 and the rostral section 84 of the medial backing piece 80 from the adhesive 44 to provide a peeled medial backing section and a non-peeled medial backing section. For example, if the rostral section 84 is peeled as depicted in FIG. 5, the peeled medial backing section is the rostral section 84 and the non-peeled medial backing section is the caudal section 82.

The medial backing piece 80 can then be folded along the pre-defined fold location 86 so that the peeled medial backing section is folded over the non-peeled medial backing section. FIG. 5 also shows a user folding the peeled medial backing section over the non-peeled medial backing section (although the pre-defined fold location 86 is not visible). If one of the caudal section 82 and the rostral section 84 of the medial backing piece 80 is longer than the other in the caudal-to-rostral dimension, then when the longer section is folded over the shorter section, the longer section projects outwardly beyond an outer boundary of the device 40 so it can easily be used as a handle to facilitate removal of the shorter section. With reference to FIG. 5, the rostral section 84 is longer than the caudal section 82 in the caudal-to-rostral dimension. Thus, when the rostral section 84 is unpeeled and folded along the pre-defined fold location 86 so that the rostral section 84 is folded over the caudal section 82, the rostral section 84 projects outwardly beyond the outer boundary of the device 40. The subsequent use of the longer section (the rostral section 84 in FIG. 5) as a handle is described below.

Figure 6:
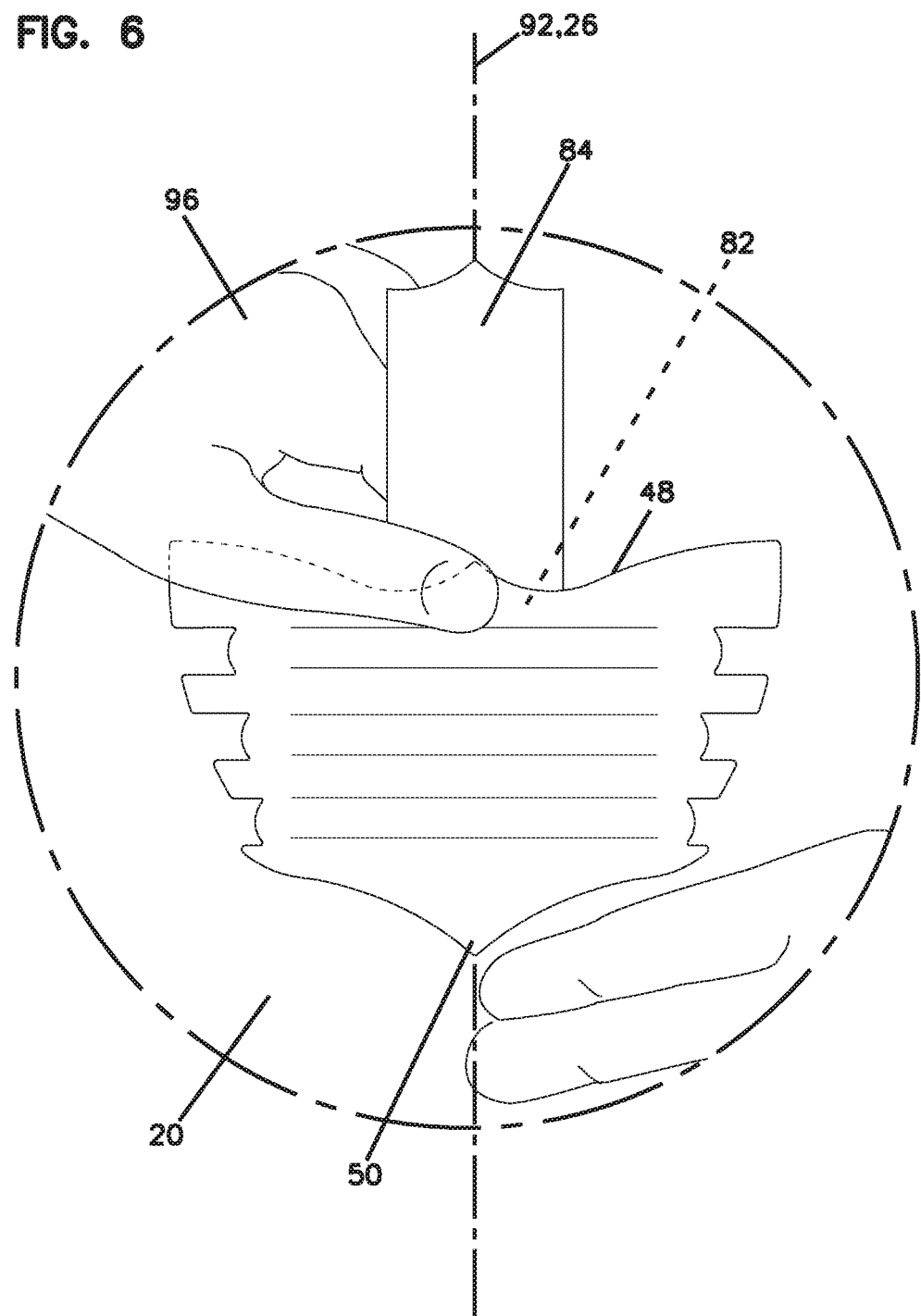
FIG. 6 shows the nasal support device of FIG. 5 being applied to the nose of the horse.

Referring to FIG. 6, the nasal support device 40 can then be grasped at a grasping location. The grasping location corresponds to the non-peeled medial backing section (the caudal section 82 in FIGS. 3 and 6) and the peeled medial backing section (the rostral section 84 in FIGS. 3 and 6) with the peeled medial backing section and the non-peeled medial backing sections being pinched together. Preferably, the grasping location is at a middle of the caudal edge 48, for example, at the reference mid-line 92 as depicted in FIG. 6.

The grasping location permits a user to position the reference mid-line 92 of the device along the reference mid-line 26 of the nose 20. The grasping location also prevents the user from touching the adhesive 44 and contaminating the adhesive 44.

Additional backing pieces 88, 90 can be peeled from the left adhesive 70 and the right adhesive 72 while the nasal support device 40 remains grasped at the grasping location. In one example, the backing pieces 88, 90 can be removed before positioning or aligning the nasal support device 110 on the nose 20.

The nasal support device 40 can then be adhered to the nose 20 while the nasal support device 40 remains grasped at the grasping location. FIG. 6 shows a user 96 adhering the device 40 to the nose 20 while grasping at the grasping location. The nasal support device 40 is preferably adhered such that the reference mid-line 92 of the device 40 is aligned along the reference mid-line 26 of the nose 20 directly over the nasal passages 32. Preferably, the rostral edge 50 of the device 40 is positioned two finger widths above the nostrils 33 prior to adhering the device 40 to the nose 20. Since one hand of the user 96 is grasping the device 40 at the grasping location, the user 96 generally uses his or her other hand to press down the device 40 and adhere a portion of the adhesive 44 to the nose 20.

Once a portion of the adhesive 44 of the nasal support device 40 has been adhered to the nose 20 (e.g., at least some of the medial adhesive 68 that was originally covered by the peeled medial backing section), a user can release his or her grasp at the grasping location and the non-peeled medial backing section can be unpeeled from the adhesive 44. For unpeeling, the peeled medial backing section can be used as a handle for unpeeling the non-peeled medial backing section from the adhesive 44. This handle is especially useful for unpeeling the non-peeled medial backing section because, at this point, a portion of the adhesive 44 is already adhered to the surface of the nose 20 and the non-peeled medial backing section of the medial backing piece 80 is adjacent to the surface of the nose 20. Absent the handle, it would be difficult to unpeel the non-peeled medial backing section. After the medial backing piece 80 has been entirely unpeeled, the remainder of the adhesive 44 corresponding to the medial portion 56 (e.g., the medial adhesive 68 that was originally covered by the non-peeled medical backing section) can then be adhered to the nose 20. This can be accomplished by pressing the device 40 down onto the nose 20 along the mid-line 92. The left adhesive 70 and right adhesive 72 can then be pressed down to adhere to the nose.

As shown in FIGS. 5 and 6, preferably the rostral section 84 of the medial backing piece 80 is the peeled medial backing section that is initially peeled and the caudal section 82 of the medial backing piece 80 is the non-peeled medial backing section that is subsequently peeled.

Figure 7:
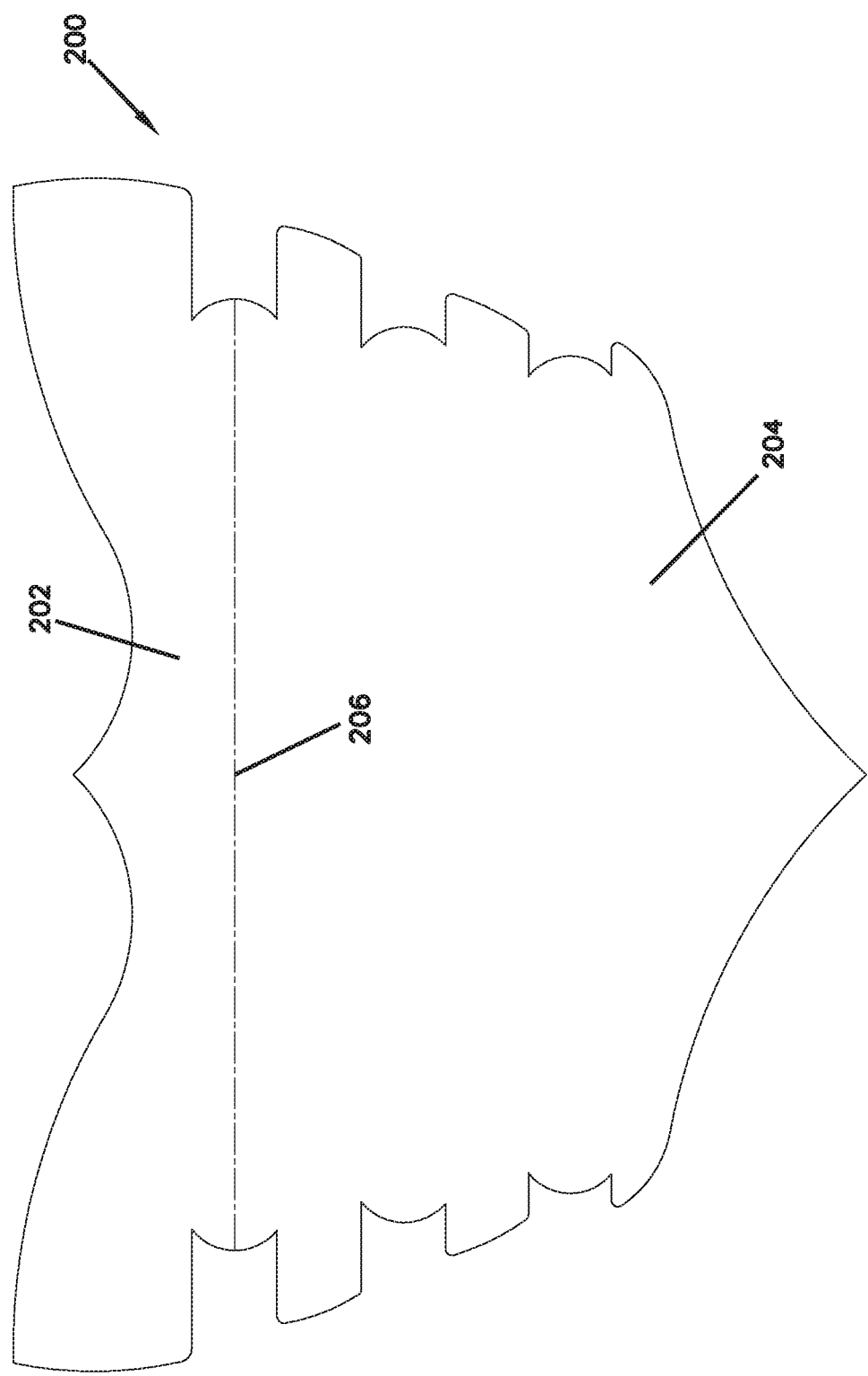
FIG. 7 shows another backing configuration for a nasal support device in accordance with the principles of the present disclosure.

FIG. 7 shows an alternative backing arrangement 200 including a one-piece construction. The backing arrangement 200 includes a caudal section 202 connected to a rostral section 204 by a pre-defined fold location 206. The fold location 206 extends from lateral edge to lateral edge of the nasal support device. The rostral section 206 has a larger area than the caudal section 202. In certain examples, the rostral section 204 has an area that is at least 2, 3 or 4 times as large as the area of the caudal section 202. In use, the rostral section 204 is initially peeled from the nasal support and pinched against the unpeeled caudal section 202 as the nasal support is positioned at the proper location on the nose. During positioning, the rostral section 204 remains intact with the caudal section 202 at the fold location 206. Once a portion of the adhesive previously covered by to the rostral section 204 has been adhered to the nose, the caudal section 202 can be unpeeled using the rostral section 204 as a handle. Thereafter, the nasal support can be fully adhered to the nose.

Adhesive

Preferably, the adhesive is biocompatible and provides minimal or no contact irritation when applied to the external tissues of an animal. Suitable materials for the adhesive are single or double coated medical tapes, transfer adhesives, liquid adhesives, pressure sensitive adhesives (PSA), etc. Examples of suitable adhesive systems include No. 1509 double sided medical tape, No. 9942 Hydrocolloid Skin Protective Adhesive and No. 1524 transfer adhesive available from 3M Co., St. Paul, Minn.

The adhesive can be continuous. Alternatively, the adhesive can be in a discontinuous pattern. A variety of patterns may be used including circles, ovals stripes, or polygons, such as rectangles, squares, triangles, etc. The pattern need not be symmetrical. In addition, the discontinuous adhesive pattern may extend to the periphery of the device or a continuous pattern adhesive border can be applied around the perimeter. In addition, two or more adhesives may be used in combination to optimize adherence under different conditions. For example, a first adhesive could provide greater adherence under dry conditions and a second adhesive could provide greater adherence under moist conditions. Holes can also be formed through the entire thickness of a nasal support device after a continuous adhesive is applied, thus forming a discontinuous adhesive layer. Preferably, the locations of the holes are selected to avoid penetration through the nasal support structure.

Without being limited to a single theory, it is believed that in addition to permitting passage of perspiration to the exterior surface of the device, the discontinuous adhesive pattern, particularly in the form of holes, facilitates malleability of the device to permit the device to more readily conform to the surface contours of the vestibular free wall of the nasal passages without loss of adherence or reduced support of the device.

Substrate Layer

The substrate layer can be visible when the device is applied to the nose of an animal. The substrate layer can be the layer farthest from the soft tissues of the animal. The substrate layer can provide additional support to the vestibular wall of the nasal passages and help maintain unity of the components of a nasal support device. The substrate layer can define an outer boundary or perimeter of the nasal support device. Suitable substrate layers are disclosed in, for example, U.S. Pat. No. 6,823,864.

Nasal Support Structure

The nasal support structure of the device provides the majority of the support for the vestibular free wall of the nasal passage. Generally, the nasal support structure comprises one or more "support members." As used herein a "support member" can be prepared from any suitable material which provides the desired support to the vestibular free wall. Examples of suitable materials for a support member include thermoplastic resins, thermoset resins, shape memory metals, alloys, etc. The support member can be an open mesh or solid material. Alternatively, the support member can be two or more individual sections of an open mesh or solid material. Suitable materials for a support member are disclosed in U.S. Pat. No. 5,913,873 and International Patent Publication WO 98/47451, which are incorporated herein by reference in their entireties.

A nasal support structure is a structural component or arrangement of structural components that functions to support the vestibular free wall of the nasal passage when applied to a nose. A structural component can include a member such as a layer, a strip, a rod, a beam, a tab, a finger, or the like. The nasal support structure can be metal or polymeric. The nasal support structure can have a neutral orientation and a flexed orientation. When the nasal support structure is flexed from the neutral orientation to the flexed orientation, the nasal support structure can deform such that an internal spring load/force is generated which biases (e.g., urges) the nasal support structure at least partially back toward the neutral orientation. In one example, the nasal support structure has a neutral orientation that is generally flat and a flexed orientation that is curved. The nasal support structure is preferably incorporated into a nasal support device. When the nasal support device is applied to a nose, the nasal support structure flexes from the neutral orientation to the flexed orientation. The nasal support device is preferably adhered to the nose with adhesive such that the nasal support structure is retained in an at least partially flexed orientation by the adhesive interface between the nasal support device and the outer surface of the nose. In this way, the internal spring load/force of the nasal support structure can act upon and apply outward forces to the nose adjacent the nasal passages such that the nasal passages are gently supported so as to resist narrowing of the nasal passages. The outward forces can be referred to as nasal passage supporting forces, nasal passage stabilizing forces, nasal passage retaining forces, nasal lifting forces or the like. The nasal support structure is configured to provide sufficient spring force or other force to effectively hold or support the nasal passages such that the narrowing of the nasal passages during breathing is reduced. This type of nasal support allows the subject to breathe more easily, particularly during physical exertion.

In some embodiments, the support members can be a generally uniform thickness throughout their length and width. The thickness of the support members can typically be selected based on the support needed, and is generally the same throughout. However, the support members can also vary in thickness in different regions of the device. In addition, a support member need not be the same width throughout its length. That is, a support member can be wider at the ends of the support member and narrower near the midline region. Alternatively, a support member can be wider near the midline region and narrower at the ends.

The support members can be positioned parallel to the transverse axis of the device and extend partially or completely to the left and right edges of the device. Three to six support members are preferred. When more than one support member is used, the width, length and spacing of the support members can vary based on the overall dimensions of the particular device.

In one embodiment using a single support member, the configuration of the peripheral edge of the support member can define the external contours of the overall device. In other embodiments, two and preferably, three or more support members are used. In such embodiments, a plurality of support members can be arranged parallel along the transverse dimension of the device. Alternatively, a plurality of support members can be oriented perpendicular to one another such that one or more support members are oriented parallel to the transverse dimension of the device and one or more support members are oriented parallel to the caudal-to-rostral orientation of the device.

When using multiple support members, the spacing between individual support members can affect the adherence and overall functioning of the device. Appropriate spacing between individual support members provides for the device to adaptively conform to the changing contours of the vestibular wall of an animal during inspiration, expiration, or other movements, without disengaging from the animal's nose. When two or more support members are used, the width of the support members and the spacing between support members are selected for the device to provide the desired support to the vestibular wall with sufficient flexibility to reduce the chance of irritation due to localized pressure at leveraging points on the animal's nose. Use of multiple support members advantageously provides for torsional flexibility of the device which facilitates function and reduces the likelihood of disengagement of the device when subjected to the unique mobility of an animal's vestibular tissues.

Definitions

A pre-defined fold location of a backing piece is a location in the backing piece that forms a preferential fold location that divides the backing piece into sections (e.g., first and second sections). The pre-defined fold location can be formed by means such as pre-folding, scoring, perforating, or other means. In a preferred example, the pre-defined fold location is a line. In another preferred example, the line defining the pre-defined fold location is straight, but could also be curved or other configuration that provides a preferential location for folding. The pre-defined fold location is configured such that the first and second sections of the backing piece separated by the pre-defined fold location remain substantially coupled together after folding and the backing piece remains intact after folding. Thus, while the pre-defined fold location forms a preferential fold location, it may not be a cut that extends fully through the thickness of the backing piece. In the case of a scored line, the line can have a depth that extends only partially through a thickness of the backing piece. In the case of a perforated line, first portions of the perforated line may extend fully or partially through the full thickness of the backing piece, while second portions extend only partially though the thickness of backing piece or do not penetrate into the thickness of the backing piece at all so that the first and second sections. In any event the pre-defined fold allows for the particular backing piece to remain coupled together after folding.

The term rostral generally refers to the portion of a nose nearer the apex of the nose.

The term caudal generally refers to the portion of a nose nearer the eyes of the subject.

A caudal edge is an edge of a nasal support device that is intended to be oriented toward the caudal end of a nose when the nasal support device is mounted on the nose.

A rostral edge is an edge of a nasal support device that is intended to be oriented toward the rostral end of a nose when the nasal support device is mounted on the nose.

A medial portion of a nasal support device is a portion that is intended to be oriented along a mid-line of a nose when the nasal support device is mounted on the nose.

A left portion of a nasal support device is a portion that is intended to be located on a left side of a nose when the nasal support device is mounted on the nose.

A right portion of a nasal support device is a portion that is intended to be located on a right side of a nose when the nasal support device is mounted on the nose.

A lateral dimension is a dimension that extends from the left edge to the right edge of the nasal support device. The lateral dimension can also be referred to as a transverse dimension.

A caudal-to-rostral dimension is a dimension that extends from the caudal edge to the rostral edge of the nasal support device.

A caudal-to-rostral orientation means an orientation that extends from the caudal edge to the rostral edge of the nasal support device.

A device body is a physical structure that defines a physical shape of the nasal support device and functions as a carrier for adhesive. The device body can include one or more components. Example components of the device body can include layers, nasal support structures, and the like. Example layers can include fabric layers. Fabrics can include knitted fabric, woven fabric, or non-woven fabric (e.g., a fabric such as a felt than is neither knitted nor woven). Example layers can also include polymeric layers such as films or sheets. In the case where the device body includes more than one component, adhesive can contact one or more of the components, but does not need to directly contact all of the components.

A substrate is a layer that can carry an adhesive that is applied to the substrate or otherwise coupled to the substrate.

What is claimed is:

1. A method for applying a nasal support device to a nose, the nasal support device comprising: a device body defining a perimeter shape of the nasal support device, the device body also including a nasal support structure; adhesive carried with the device body; and a peelable backing that covers the adhesive, the peelable backing including at least one peelable backing piece that is divided into a first section and a second section by a pre-defined fold location, the pre-defined fold location being configured such that the first and second sections of the peelable backing piece remain coupled together at the pre-defined fold location after folding at the pre-defined fold location, the method comprising: peeling the first section of the peelable backing piece from the adhesive of the nasal support device;

folding the peelable backing piece along the pre-defined fold location such that the first section of the peelable backing piece is folded over the second section of the peelable backing piece;

grasping the nasal support device at a grasping location where the first and second sections of the peelable backing piece are pinched together;

adhering a first portion of the adhesive of the nasal support device corresponding to the first section of the peelable backing piece to the nose while the nasal support device remains grasped at the grasping location;

once the first portion of the adhesive of the nasal support device has been adhered to the nose, releasing grasp from the nasal support device at the grasping location and unpeeling the second section of the peelable backing piece from the adhesive, wherein the first section of the peelable backing piece is used as a handle for unpeeling the second section of the peelable backing piece from the adhesive; and adhering a second portion of the adhesive of the nasal support device corresponding to the second section of the peelable backing piece to the nose after the peelable backing piece has been entirely unpeeled.

2. The method of claim 1, wherein the device body includes a rostral edge and a caudal edge, wherein the first section of the peelable backing piece is adjacent to the rostral edge and the second section of the peelable backing piece is adjacent to the caudal edge, and wherein the nasal support device is applied to the nose with the caudal edge oriented toward a caudal end of the nose and the rostral edge is oriented toward a rostral end of the nose.

3. The method of claim 2, wherein a mid-line of the nasal support device extends in a caudal-to-rostral orientation between the caudal edge and the rostral edge, wherein peelable backing piece is located at the mid-line and the pre-defined fold location extends along a fold line perpendicular to the mid-line, wherein the first section of the peelable backing piece is longer than the second section of the peelable backing piece in the caudal-to-rostral orientation, and wherein the first section extends past the caudal edge in a caudal direction once the peelable backing piece has been folded.

4. The method of claim 3, wherein the backing has a one piece construction that includes only the peelable backing piece.

5. A method for applying a nasal support device to a nose, the nasal support device comprising: a device body defining a perimeter shape of the nasal support device, the perimeter shape including a caudal edge and a rostral edge, the device body also including a nasal support structure, the device body having a mid-line which extends in a caudal-to-rostral orientation between the caudal edge and the rostral edge; adhesive carried with the device body; and a peelable backing that covers the adhesive, the peelable backing including at least one peelable backing piece that is divided into a first section and a second section by a pre-defined fold location, the pre-defined fold location being configured such that the first and second sections of the peelable backing piece remain coupled together at the pre-defined fold location after folding at the pre-defined fold location, the peelable backing piece being located at the mid-line, the first section of the peelable backing piece being longer than the second section of the peelable backing piece in the caudal-to-rostral orientation, the first section of the peelable backing piece being adjacent to the rostral edge of the perimeter shape and the second section of the peelable backing piece being adjacent to the caudal edge of the perimeter shape, and wherein the device body is configured such that in use on a nose the caudal edge is oriented toward a caudal end of the nose and the rostral edge is oriented toward a rostral end of the nose; the method comprising: peeling the first section of the peelable backing piece from the adhesive of the nasal support device;

folding the peelable backing piece along the pre-defined fold location such that the first section of the peelable backing piece is folded over the second section of the peelable backing piece;

grasping the nasal support device at a grasping location where the first and second sections of the peelable backing piece are pinched together;

adhering a first portion of the adhesive of the nasal support device corresponding to the first section of the peelable backing piece to the nose while the nasal support device remains grasped at the grasping location;

once the first portion of the adhesive of the nasal support device has been adhered to the nose, releasing grasp from the nasal support device at the grasping location and unpeeling the second section of the peelable backing piece from the adhesive, wherein the first section of the peelable backing piece is used as a handle for unpeeling the second section of the peelable backing piece from the adhesive; and adhering a second portion of the adhesive of the nasal support device corresponding to the second section of the peelable backing piece to the nose after the peelable backing piece has been entirely unpeeled.

* * * * *